(12) United States Patent
Oliver

(10) Patent No.: US 9,949,509 B2
(45) Date of Patent: *Apr. 24, 2018

(54) SWEATSHIRT PIPE AND ATTACHMENTS

(71) Applicant: Sean Oliver, Santa Cruz, CA (US)

(72) Inventor: Sean Oliver, Santa Cruz, CA (US)

( * ) Notice: Subject to any disclaimer, the term of this patent is extended or adjusted under 35 U.S.C. 154(b) by 96 days.

This patent is subject to a terminal disclaimer.

(21) Appl. No.: 14/545,031

(22) Filed: Mar. 18, 2015

(65) Prior Publication Data

US 2015/0196061 A1    Jul. 16, 2015

Related U.S. Application Data

(63) Continuation-in-part of application No. 13/986,240, filed on Apr. 15, 2013, now Pat. No. 9,339,064.

(51) Int. Cl.
| | | |
|---|---|---|
| *A24F 47/00* | (2006.01) | |
| *A42B 1/04* | (2006.01) | |
| *A61L 9/03* | (2006.01) | |
| *A41D 1/04* | (2006.01) | |

(52) U.S. Cl.
CPC .............. *A24F 47/008* (2013.01); *A41D 1/04* (2013.01); *A42B 1/048* (2013.01); *A61L 9/03* (2013.01); *A41D 2200/20* (2013.01)

(58) Field of Classification Search
CPC ...... A24F 47/008; A41D 31/0022; A41D 1/04
USPC ................................................. 2/84; 131/178
See application file for complete search history.

(56) References Cited

U.S. PATENT DOCUMENTS

| | | |
|---|---|---|
| 1,727,763 A | 9/1929 | Gevirman |
| 1,926,866 A | 7/1932 | Doniger et al. |
| 2,078,844 A | 8/1936 | Gardian |
| 4,094,508 A | 6/1978 | Kirsch |
| 4,243,058 A | 1/1981 | Gershbein |
| 4,681,244 A | 7/1987 | Geddie |
| 5,685,015 A | 11/1997 | Aldridge |
| 7,519,192 B1 | 4/2009 | Laycock et al. |
| D627,540 S * | 11/2010 | Claeys ........................... D2/750 |
| 8,082,753 B1 * | 12/2011 | Alvarez, Jr. .............. A45F 3/16 224/148.1 |
| 8,393,013 B2 * | 3/2013 | Bowen .................... A41D 15/04 2/69 |
| 2005/0035160 A1 * | 2/2005 | Forsman ................... A45F 3/14 224/148.2 |
| 2007/0012732 A1 * | 1/2007 | Adams ..................... A01K 7/00 224/148.2 |

(Continued)

OTHER PUBLICATIONS

Fleece Sweatshirt, Nomex IIIA. Bulwark Web. Feb. 13, 2015. Retrieved Nov. 16, 2011. http://www.bulwark.com/p-255-fleece-sweatshirt-nomex-iiia-navy.aspx.

(Continued)

*Primary Examiner* — Richale Quinn
*Assistant Examiner* — Anne Kozak
(74) *Attorney, Agent, or Firm* — Haverstock & Owens LLP

(57) ABSTRACT

A sweatshirt having a smoking apparatus as part of the sweatshirt, allowing users to smoke out of the sweatshirt comprises a garment body having a neck opening and sleeves and an elongated cord for tightening the sweatshirt hood around the users head and neck. A hollow tube is positioned inside of the elongated cord. The elongated tube has a smoking apparatus secured thereto which may be a pipe, a vaporizer, an atomizer, a pre-filled electronic cigarette or other apparatus for smoking.

9 Claims, 5 Drawing Sheets

(56) References Cited

U.S. PATENT DOCUMENTS

| | | | |
|---|---|---|---|
| 2007/0028359 A1* | 2/2007 | Robinson | A42B 1/048 |
| | | | 2/171 |
| 2007/0094763 A1 | 5/2007 | Silver | |
| 2009/0019624 A1* | 1/2009 | Birk | D02G 3/443 |
| | | | 2/455 |
| 2009/0288670 A1 | 11/2009 | Lee et al. | |
| 2010/0326453 A1* | 12/2010 | Chaoui | A24F 1/30 |
| | | | 131/173 |
| 2012/0045084 A1 | 2/2012 | Groset et al. | |
| 2013/0247271 A1* | 9/2013 | Bowen | A41D 1/00 |
| | | | 2/144 |
| 2013/0269717 A1* | 10/2013 | Raouf | A24F 7/02 |
| | | | 131/202 |
| 2014/0047614 A1* | 2/2014 | Becton | A41D 1/00 |
| | | | 2/84 |
| 2014/0053854 A1* | 2/2014 | Barry, Jr. | A24F 47/00 |
| | | | 131/178 |
| 2016/0015104 A1* | 1/2016 | Edwards | A41D 1/002 |
| | | | 2/94 |

OTHER PUBLICATIONS

FR Nomex Jackets. Bulwark Web. Feb. 19, 2015. Retrieved Nov. 29, 2011. http://www.bulwarkonline.com/c-30-fr-nomex-jeackets.aspx.

* cited by examiner

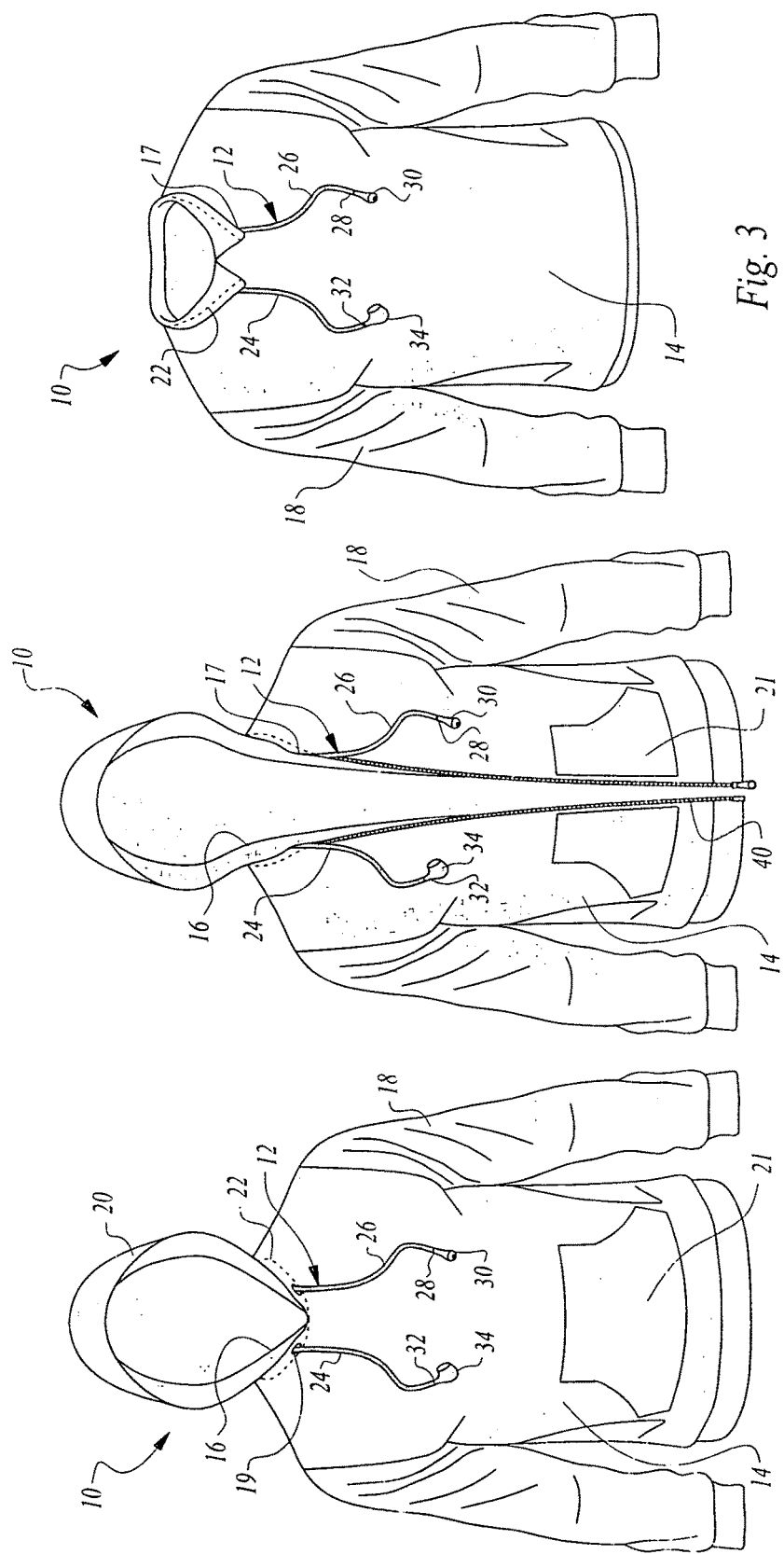

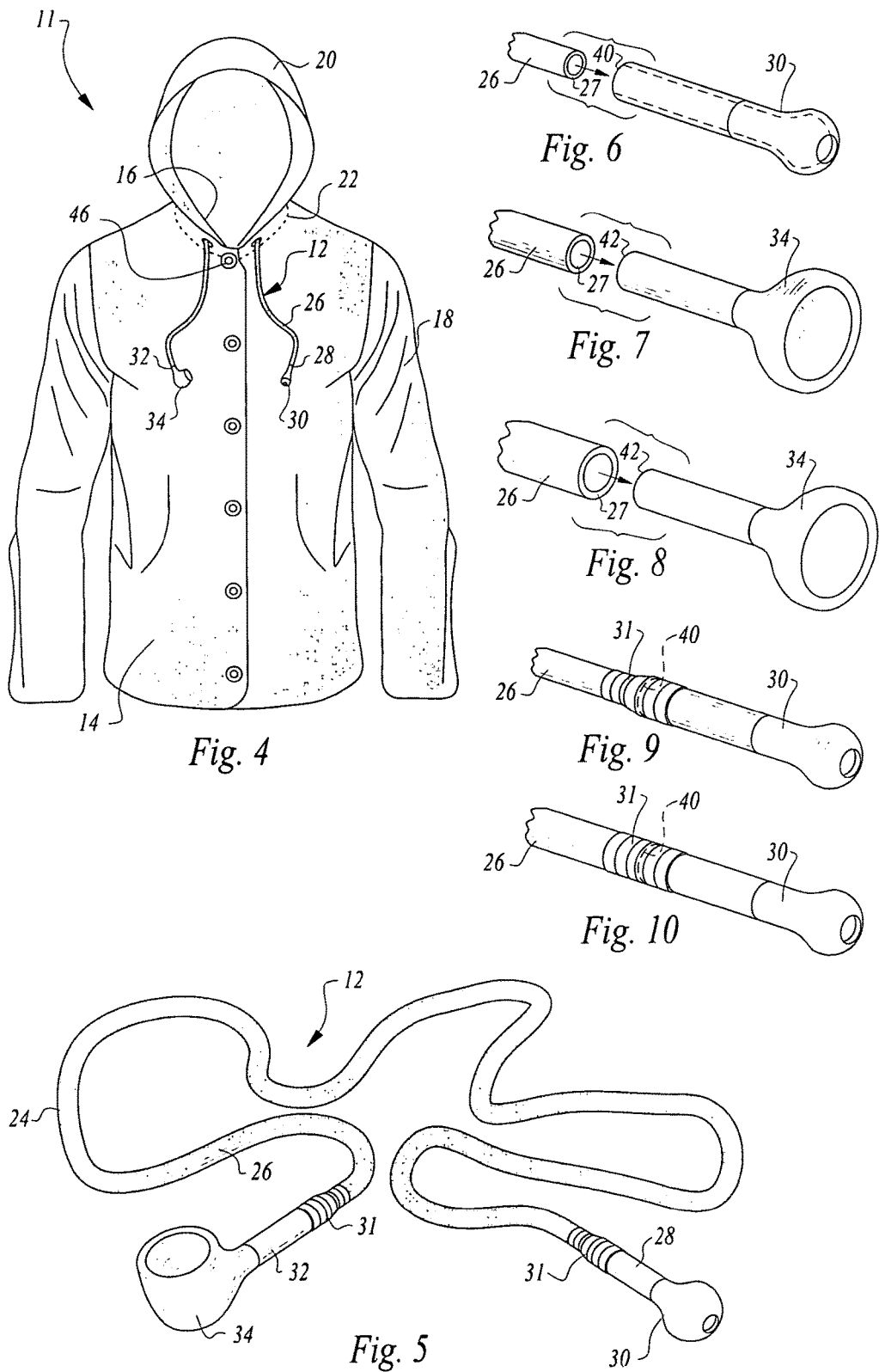

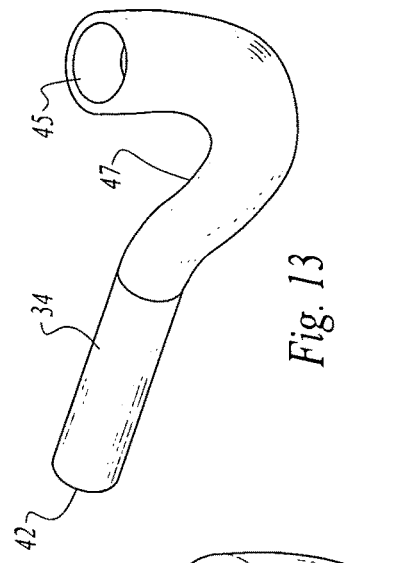
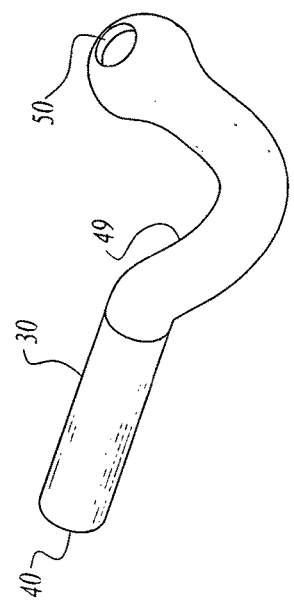
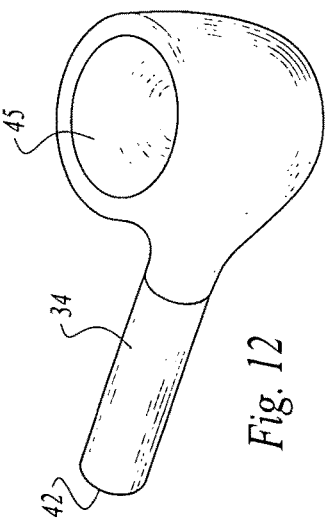
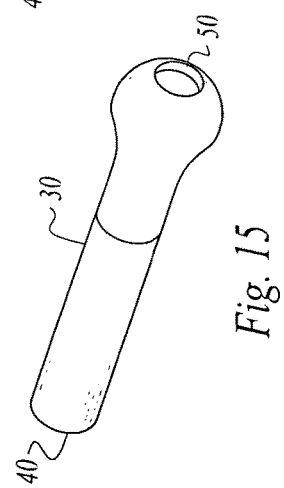
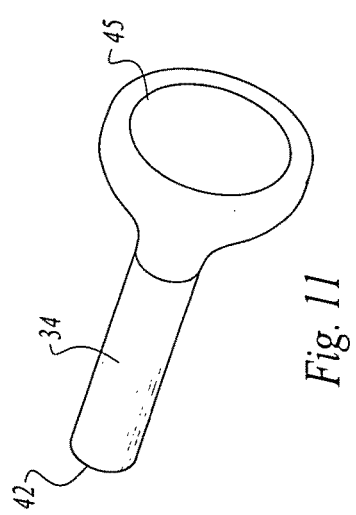
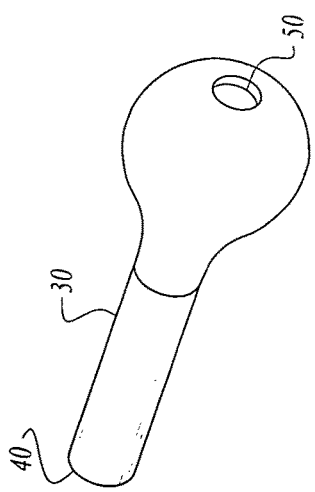
Fig. 11
Fig. 12
Fig. 13
Fig. 14
Fig. 15
Fig. 16

SWEATSHIRT PIPE AND ATTACHMENTS

CROSS REFERENCE TO RELATED APPLICATIONS

This patent application is a continuation-in-part of and claims priority from co-pending patent application Ser. No. 13/986,240 filed Apr. 15, 2013, and is related to and claims priority from PCT International Patent Application PCT/US2014/000035 filed Mar. 13, 2014.

BACKGROUND OF THE INVENTION

Technical Field

This invention relates generally to garments, and more particularly to a hooded garment such as a sweatshirt having a smoking apparatus as a part of the clothing, allowing a user to smoke out of their clothes. More particularly, this invention relates to hooded garments such as sweatshirts and jackets with a smoking apparatus which may be a pipe-type apparatus, a vaporizer, an atomizer, an e-cig or electronic cigarette, or other apparatuses used for smoking tobacco and other substances.

Background Art

Various types of clothing have been proposed and implemented which use cords or strings to close a portion thereof. Well known examples are sweatshirts, hooded sweatshirts, sweaters, jackets and pants. Although a wide variety of such clothing has been proposed and implemented for normal wear and use as well as for sport and recreational purposes, the present invention provides a novel and unique sweatshirt which may be used both as a sweatshirt and a smoking apparatus. Although prior sweatshirts have been adapted and used for various purposes, there have not been developments in the sweatshirt field that allow a user to use the sweatshirt to safely smoke for either pleasure or medicinal purposes. Accordingly, the present invention shares very little with existing sweatshirts, and has a completely different utility and effect.

Since the advent of human history, humans have worn various types of clothing to protect themselves from the elements. Some of these clothing have been directed to a cold weather climate, while others to warmer conditions, and others to moderated or intermediate temperature conditions.

It is well known in the art that many types of cool or cold weather apparel exist for protecting a wearer's body, especially, the upper torso, including coats, sweaters, sweatshirts, and other related outerwear. In many cases, different items of apparel may be worn together, such as a coat and a hat to improve the overall protection and utility for the wearer. Similarly, certain apparel may combine features such as a coat liner or removable hood, to increase the circumstances in which the apparel might be appropriately used.

In addition to separate apparel, in some designs, outerwear may include combinations of protective elements in an integrated design. For example, some coats, jackets, sweatshirts, and sweaters, include a hood which is integrally formed or is removable. This allows the user to cover the head and neck when exposed to the elements and lower or remove the hood when not needed.

The present invention, provides, for the first time, a sweatshirt which may be hooded or not, which has a smoking apparatus as an integral part thereof. The sweatshirt of the present invention allows a user to safely and conveniently smoke without the need of a separate device or apparatus. This is something that a conventional sweatshirt is unable to do, but is done with ease on the sweatshirt of the present invention.

The sweatshirt of the present invention also possesses the ability to allow users to smoke easily and safely in an article of clothing being worn by the user and is configured to be highly adaptable to any style, type or design of sweatshirt.

The present invention provides a unique smoking sweatshirt that is both comfortable, utilitarian, and practical. The applicant is not aware of any other sweatshirt construction or design that so allows a user to smoke directly from the sweatshirt while being worn by the user.

Accordingly, the primary object of the present invention is to provide a smoking sweatshirt which may be used and worn like a conventional sweatshirt, but which has a smoking apparatus integral therewith, allowing the wearer enjoy a smoke while wearing the sweatshirt. The sweatshirt of the present invention is easily adapted for use, is easy to learn how to use, is very reliable, safe, and is very efficient in operation.

Another object of the present invention is to provide a hooded garment such as a sweatshirt having a smoking apparatus as a part of the clothing, allowing a user to smoke out of their cloths. The smoking apparatus may be a pipe-type apparatus, a vaporizer, an atomizer, an e-cig or electronic cigarette or other apparatuses used for smoking tobacco and other substances.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF SUMMARY OF THE INVENTION

To achieve the foregoing objects, and in accordance with the purpose of the invention as embodied and broadly described herein, a sweatshirt pipe having a smoking apparatus integral with and as part of the sweatshirt, allows users to smoke out of the sweatshirt, comprises a garment body having a neck opening and sleeves and an elongated cord for tightening the sweatshirt hood around the users head and neck. A hollow tube is positioned inside of the elongated cord. The elongated tube has a first end and a second end with the first end having a mouthpiece, and the second end having a smoking bowl for retaining smoking material. In various embodiments the sweatshirt may be hooded or not, designed with any choice of color, and made in any style or design. The elongated cord may be string composed of cloth, cord, or other tubing, which functions both as a smoke conduit and a tightening element of the sweatshirt. The mouthpiece may be provided in various configurations and designs and is constructed of a heat resistant material. The smoking bowl may be provided in various configurations and designs and is composed of a heat resistant material. The elongated tube is secured to the mouthpiece and to the smoking bowl by a bonding agent, such as adhesives, glue, tape sealant, heat shrink-type attachment, or the like. The sweatshirt, garment body, neck opening and sleeves, and hood, if provided, are preferably composed of a heat resistant, fireproof material capable of withstanding high temperatures. This invention also contemplates hooded garments such as sweatshirts and jackets with a smoking apparatus which may be a pipe-type apparatus or other attachments such as a vaporizer, an atomizer, an e-cig or electronic cigarette, a pre-filled e-cigarette, or other apparatuses used for smoking tobacco and other substances. Accordingly, the present invention provides a sweatshirt pipe, which functions both as a sweatshirt and a smoking apparatus. The present invention contemplates the use of the present invention with other clothing types such as jackets, sweaters, and the like.

BRIEF DESCRIPTION OF THE DRAWINGS

The accompanying drawings, which are incorporated in and constitute a part of the specification, illustrate a preferred embodiment of the invention and, together with a general description given above and the detailed description of the preferred embodiment given below, serve to explain the principles of the invention.

FIG. 1, shows a sweatshirt pipe having a smoking apparatus as part of the sweatshirt, allowing users to smoke out of the sweatshirt, according to the invention.

FIG. 2, shows zippered sweatshirt pipe having a smoking apparatus as part of the sweatshirt, allowing users to smoke out of the sweatshirt, according to the invention.

FIG. 3, shows a sweatshirt without a hood having a smoking apparatus as part of the sweatshirt, allowing users to smoke out of the sweatshirt, according to the invention.

FIG. 4, shows a winter style coat with the sweatshirt pipe as part of the coat, allowing users to smoke out of the coat, according to the invention FIG. 5, shows an elongated cord or covered tubing which functions as both a drawstring for the sweatshirt and a smoking device, according to the invention.

FIG. 6, shows a preferred connection of the covered tubing with a smoking mouthpiece or bowl, where the tubing is smaller than the mouthpiece, according to the invention.

FIG. 7, shows another a preferred connection of the covered tubing with a smoking mouthpiece or bowl where the tubing is the same size as the mouthpiece, according to the invention.

FIG. 8, shows another a preferred connection of the covered tubing with a smoking mouthpiece or bowl where the tubing is larger in size than the mouthpiece, according to the invention.

FIG. 9, shows a preferred way to seal the tubing to the mouthpiece or bowl using silicone tape, according to the invention.

FIG. 10, shows another preferred way to seal the tubing to the mouthpiece or bowl where the tips of both the tubing and the mouthpiece or bowl are glued together, according to the invention.

FIG. 11, shows a preferred bowl shape for the smoking apparatus, according to the invention.

FIG. 12, shows another preferred bowl shape for the smoking apparatus, according to the invention.

FIG. 13, shows another preferred bowl shape for the smoking apparatus, according to the invention.

FIG. 14, shows a preferred mouthpiece shape for the smoking apparatus, according to the invention.

FIG. 15, shows another preferred mouthpiece shape for the smoking apparatus, according to the invention.

FIG. 16, shows another preferred mouthpiece shape for the smoking apparatus, according to the invention.

DETAILED DESCRIPTION OF THE INVENTION

Figure 18:
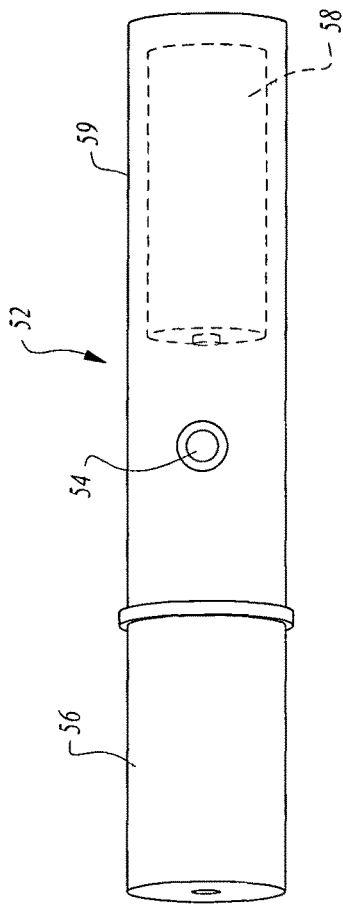
FIG. 18, shows the vaporizer of FIG. 17, detached from sweatshirt 10, according to the invention.

Reference will now be made in detail to the present preferred embodiments of the invention as illustrated in the accompanying drawings.

In accordance with the present invention, there is provided in a preferred embodiment of the invention, a sweatshirt having a smoking apparatus as part of the sweatshirt, allowing users to smoke out of the sweatshirt. The sweatshirt comprises a garment body having a neck opening and sleeves and an elongated cord for tightening the sweatshirt hood or neck around the users head and neck. A hollow tube is positioned inside of the elongated cord. Preferably the elongated tube has a first end and a second end with the first end having a mouthpiece, and the second end having a smoking bowl for retaining smoking material. The smoking apparatus may be a pipe, a vaporizer, an atomizer, an e-cigarette or e-cig, a pre-filled e-cigarette, or other smoking apparatuses and attachments well known in the art.

In FIG. 1, a preferred embodiment of a hooded sweatshirt 10, having a smoking apparatus 12, is shown, comprising, a garment body 14, having a neck opening 16, and sleeves 18. A hood 20, adapted to be worn over a user's head, is preferably attached by hood stitching 22, to the garment body 14. Hood 20, preferably has an elongated cord or drawstring 24, positioned in aperture 19, for tightening the sweatshirt hood 20, around the users head and neck. A hollow tube 26, is positioned inside of elongated cord 24. The hollow tube 26, has a first end 28, and a second end 32. The first end having a mouthpiece 30, and the second end having a smoking bowl piece 34, for retaining smoking material, such as tobacco. A front pocket 21, may be provided for the sweatshirt, as is well known in the art.

The sweatshirt 10, which may be hooded, as seen in FIGS. 1-2, has an elongated tube 26, positioned inside elongated cord or drawstring 24, which preferably is a string or drawstring composed of cloth or fibers of different materials including cotton, polyester, cotton-poly blends, fiberglass, carbon fiber, aramid, and the like, the criteria being that the material is fire resistant and fireproof.

The hollow tube 26, is preferably elongated and is composed of high temperature tubing which is covered by cord or drawstring 24. Tube 26, may be inserted into covering cord or drawstring 24, or can be pre-made with the covering. Tube 26, can be made of silicone, PVC, Tygon and other high temperature tubing well known in the art. Tubing 26, is secured at first end 28, to mouthpiece 30, by a bonding agent or other attachment mechanism, and at second end 32, to smoking bowl piece 34, by bonding agents or other attachment mechanisms. Tube 26, and covering 24, may be held in place by tube stitching 17, running the perimeter of hood 20.

Smoking bowl piece 34, is composed of a durable heat resistant, strong and shatter resistant material, such as glass, metal, wood, clay, bone, or other high temperature resilient materials. Smoking bowl piece 34, may be shaped in many different shapes, which are for the purpose of containing tobacco or other smoking material. Smoking bowl 34, can be shaped to look like a normal part of sweatshirt 10, or can be shaped to be noticed and extravagant.

Mouthpiece 30, can be made of the same materials as smoking bowl piece 34, The mouthpiece is constructed of a heat resistant material such as glass, metal, wood, clay, bone, or other high temperature resilient material, and can be made to match the appearance of smoking bowl piece 34, or otherwise. Both mouthpiece 30, and smoking bowl piece 34, can be provided in a wide variety of designs and colors.

Sweatshirt 10, may be hooded as shown in FIGS. 1-2, or provided without a hood as seen in FIG. 3. Sweatshirt 10, garment body 14, sleeves 18, and hood 20, are preferably composed of a heat resistant, fireproof material capable of withstanding high temperatures. This is also the case with the coat embodiment shown in FIG. 4, or any other article of clothing in which the present invention may be implemented, particularly those which use cords or drawstrings to tighten a part of the clothing to a part of the user's body.

With reference now to FIG. 2, a hooded sweatshirt similar to that seen in FIG. 1, is shown, except that in FIG. 2, sweatshirt 10 has a zipper 40. In FIG. 2, smoking apparatus 12, is shown, along with a garment body 14, having a neck opening 16, and sleeves 18. A hood 20, adapted to be worn over a user's head, is preferably attached by stitching 22, to the garment body 14. Hood 20, preferably has an elongated cord or drawstring 24, for tightening the sweatshirt hood 20, around the users head and neck. A hollow tube 26, is positioned inside of elongated cord 24. The hollow tube 26, has a first end 28, and a second end 32. The first end having a mouthpiece 30, and the second end having a smoking bowl piece 34, for retaining smoking material, such as tobacco.

In FIG. 3, a sweatshirt 10, similar to that seen in FIG. 1, is shown, except without a hood. In FIG. 3, smoking apparatus 12, is shown integral with sweatshirt 10. Sweatshirt 10, having a garment body 14, having a neck opening 16, and sleeves 18. Smoking apparatus 12, preferably comprises hollow tube 26, positioned inside of elongated cord 24. The hollow tube 26, has a first end 28, and a second end 32. The first end having a mouthpiece 30, and the second end having a smoking bowl piece 34, for retaining smoking material, such as tobacco. Stitches 17, are seen in FIG. 3, holding smoking apparatus 12, positioned in place, functioning both as a smoking apparatus and a drawstring for the sweatshirt.

In FIG. 4, another embodiment of smoking sweatshirt 10, is shown, here in a style as a winter coat 11, with buttons, clasps, or snaps, 46, for securely closing and buttoning the coat. In FIG. 4, smoking apparatus 12, is shown, with the coat having a garment body 14, having a neck opening 16, and sleeves 18. A hood 20, adapted to be worn over a user's head, is preferably attached by stitching 22, to the garment body 14. Hood 20, preferably has an elongated cord or drawstring 24, for tightening the sweatshirt hood 20, around the users head and neck. A hollow tube 26, is positioned inside of elongated cord 24. The hollow tube 26, has a first end 28, and a second end 32. The first end having a mouthpiece 30, and the second end having a smoking bowl piece 34, for retaining smoking material, such as tobacco.

With reference now to FIG. 5, smoking apparatus 12, comprising elongated cord or drawstring 24, hollow tube 26, mouthpiece 30, and smoking bowl piece 34, are shown taken out of sweatshirt 10, to illustrate more clearly the apparatus. Smoking apparatus 12, is preferably constructed by positioning tube 26, within cord or drawstring 24. As discussed above, cord or drawstring 24, is preferably an elongated cord, sting, or drawstring, composed of heat resistant cloth or fibers of different materials including cotton, polyester, cotton-poly blends, fiberglass, carbon fiber, aramid, and the like. The hollow tube 26, is preferably elongated and is composed of high temperature resistant and non-flammable tubing which is covered by the cord or drawstring 24. Tube 26, may be inserted into covering cord or drawstring 24, or can be pre-made with the covering. Tube 26, can be made of silicone, PVC, Tygon and other high temperature tubing well known in the art. Tubing 26, is secured at first end 28, to mouthpiece 30, by a bonding agent or other attachment mechanism, and at second end 32 to smoking bowl piece 34, by bonding agents or other attachment mechanisms. Tube 26 and covering 24, may be held in place by stitching 17, running the perimeter of hood 20, seen in FIGS. 1 and 3. In FIG. 5, smoking bowl piece 34, is seen secured to second end 32 of tube 26, and is preferably composed of a durable heat resistant, strong and shatter resistant material, such as glass, metal, wood, clay, bone, or other high temperature resilient materials. Smoking bowl piece 34, may be shaped in many different shapes, as seen in FIGS. 11-13 which are for the purpose of containing tobacco or other smoking material. Smoking bowl piece 34, can be shaped to look like a normal part of sweatshirt 10, or coat 11, or can be shaped to be noticed and extravagant. In FIG. 5, mouthpiece 30, can be made of the same materials as smoking bowl 34, The mouthpiece is constructed of a heat resistant material such as glass, metal, wood, clay, bone, or other high temperature resilient materials, and can be made to match the appearance of smoking bowl piece 34, or otherwise. Both mouthpiece 30, and smoking bowl piece 34, can be provided in a wide variety of designs and colors. In FIG. 5, both mouthpiece 30, and smoking bowl 34, are positioned and secured with a tape, such as silicone tape 31, but may be otherwise secured as discussed in relation to FIGS. 6-8.

In FIGS. 6-8 different preferred embodiments of ways to connect tube 26, with either mouthpiece 30 or smoking bowl piece 34, are shown. In FIGS. 6-8 tubing 26 is shown in various configurations to connect with either smoking bowl piece 34, or mouthpiece 30, however, the exact same variations may be used with the smoking bowl piece 34, or the mouthpiece 30.

In FIG. 6, in a preferred embodiment opening 27, in tubing 26, is configured to be smaller than opening 40, in mouthpiece 30, and can be fit into opening 40, and then sealed using a securing element such as tape, adhesives, mechanical means, or sealants. For example, silicone tape, adhesives, heat shrinking tubing strips, metal wire wraps or any other technique which is secure and creates an aesthetically appealing look may be used to secure the tubing to the mouthpiece 30 or smoking bowl piece 34. This also creates a place for the user to hold the mouthpiece or smoking bowl piece in a way which defers heat to their fingers.

In FIG. 7, in another preferred embodiment of the invention opening 27, in tubing 26, is configured to be the same size as opening 42, in smoking bowl 34, and can be fit onto opening 42, and then sealed using a securing element such as tape, adhesives, mechanical means, or sealants. For example, silicone tape, adhesives, heat shrinking tubing strips, metal wire wraps or any other technique which is secure and creates an aesthetically appealing look may be used to secure the tubing to the smoking bowl 34, or mouthpiece 30.

In FIG. 8, in another preferred embodiment of the invention opening 27, in tubing 26, is configured to be the larger in size as opening 42, in smoking bowl piece 34, and can be fit over opening 42. and then sealed using a securing element such as tape, adhesives, mechanical means, or sealants. For example, silicone tape, adhesives, heat shrinking tubing strips, metal wire wraps or any other technique which is secure and creates an aesthetically appealing look may be used to secure the tubing to the smoking bowl 34, or mouthpiece 30.

In FIGS. 9 and 10, different methods of sealing tubing 26 at either the mouthpiece 30, or smoking bowl piece 34, are shown. In FIGS. 9 and 10, the different methods are illustrated using the mouthpiece 30, however, the exact same methods may be used with the smoking bowl piece 34, as well.

With reference to FIG. 9, silicone tape 31, is used to seal tubing 26, to mouthpiece 30. In FIG. 9 tube 26, is configured smaller than opening or aperture 40, in mouthpiece 30, and silicone tape is wrapped around both. Other sealants may also be used, such as adhesives, for example, gluing tube 26, to the mouthpieces, or using heat shrink tubing strips, metal wire, or other fastening techniques well known in the art, to make an airtight seal.

In FIG. 10, another preferred method of sealing tubing 26, to either mouthpiece 30, or smoking bowl piece 34, is shown. With reference to FIG. 10, silicone tape 31, is used to seal tubing 26, to mouthpiece 30. In FIG. 10, tube 26, is configured the same size as the opening or aperture 40, in mouthpiece 30, and silicone tape is wrapped around both. However, other sealants may also be used, such as adhesives, for example, gluing tube 26, to the mouthpieces, or using heat shrink tubing strips, metal wire, or other fastening techniques well known in the art.

In FIGS. 11-13 different configurations of smoking bowl piece 34, are illustrated. It is clear that a wide variety of other smoking bowl piece configurations may be used and implemented and the configurations shown in FIGS. 11-13 are for example only.

With reference to FIG. 11, smoking bowl piece 34, with aperture 42, is shown with smoking bowl 45, positioned essentially in an upright orientation.

With reference to FIG. 12, smoking bowl piece 34, with aperture 42, is shown with smoking bowl 45, positioned essentially in an essentially horizontal orientation.

With reference to FIG. 13, smoking bowl piece 34, having a curved portion 47, with aperture 42, and is shown with smoking bowl 45, positioned in an essentially horizontal orientation.

In FIGS. 14-16, different configurations of mouthpiece 30, are illustrated. It is clear that a wide variety of other mouthpiece configurations may be used and implemented and the configurations shown in FIGS. 14-16 are for example only.

With reference to FIG. 14, mouthpiece 30, with opening or aperture 40, is shown with inhalation opening 50, positioned essentially in an upright orientation.

With reference to FIG. 15, mouthpiece 30, with opening or aperture 40, is shown with inhalation opening 50, positioned in an essentially horizontal orientation. This configuration, as with FIGS. 9 and 10, illustrates in a generic manner the application of an attachment such as an vaporizer, an atomizer, or an e-cigarette type smoking apparatus.

With reference to FIG. 16, smoking bowl piece 34, having a curved portion 49, with an opening or aperture 42, and is shown with inhalation opening 50, positioned in an essentially horizontal orientation.

Figure 17:
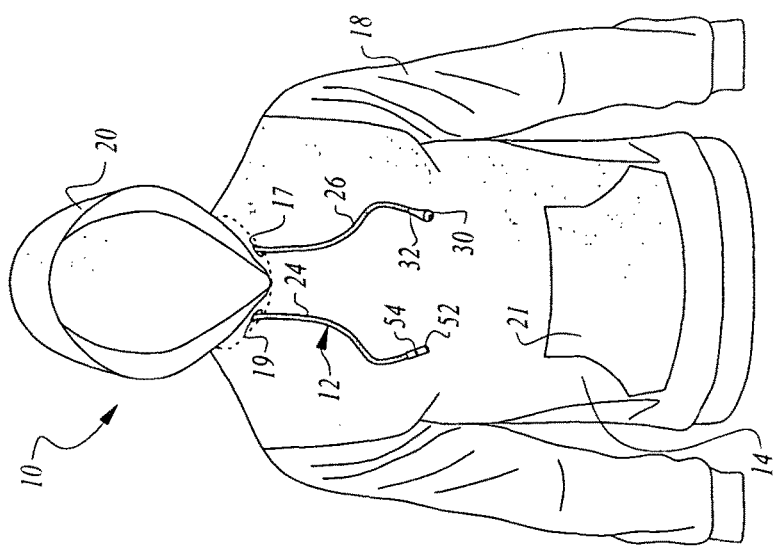
FIG. 17, shows another embodiment of the invention where a vaporizer is used as a smoking apparatus, according to the invention.

In FIG. 17, another embodiment of the invention is shown where the smoking apparatus 12, is a vaporizer 52, for smoking concentrates of tobacco, or other smoking material. In FIG. 17, sweatshirt pipe 10, has a vaporizer 52, with on/off button 54, and mouthpiece 30, operably secured thereto.

With reference to FIG. 18, vaporizer 52 is shown detached from sweatshirt pipe 10, with mouthpiece/cover 56, on/off button 54, and battery housing 58, for a battery 59.

Figure 19:
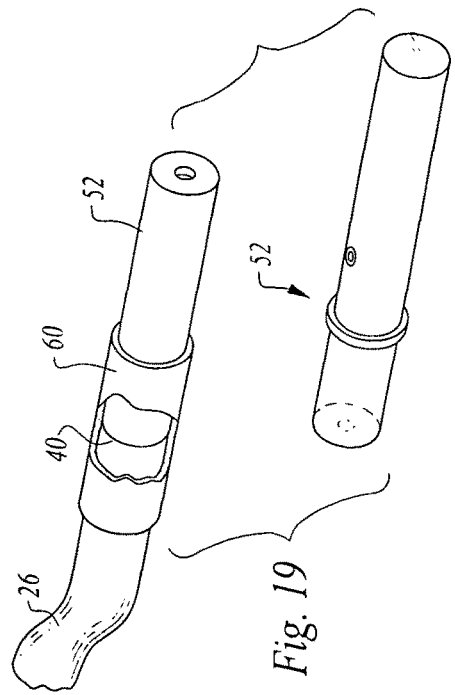
FIG. 19, shows a means to secure a vaporizer to sweatshirt 10, according to one embodiment of the invention.

In FIG. 19, illustrates a means to secure vaporizer 52, and/or mouthpiece 30, to tubing 26, which is preferably a high temperature resilient tube, by using a securing element such as heat shrink material 60, to secure and bind vaporizer 52, and mouthpiece 30, to their respective ends of tube 26. Of course, other fastening means may also be used such as adhesives, bonding agents, tape, or the like.

Figure 20:
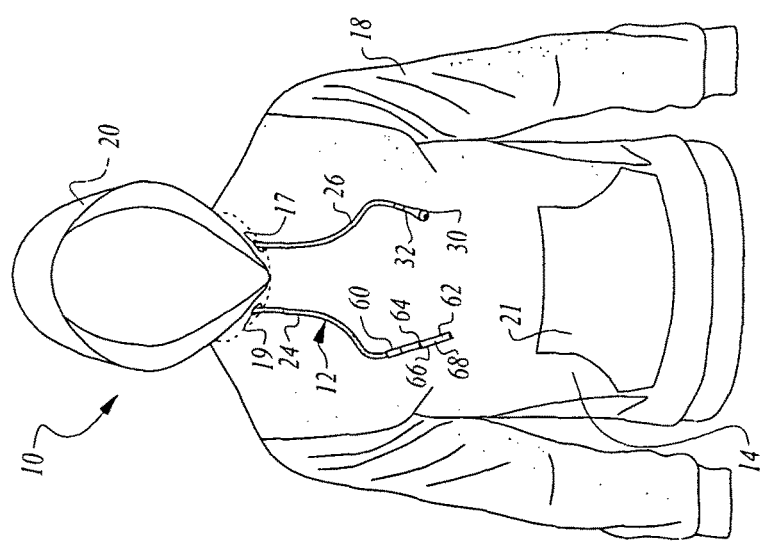
FIG. 20, shows another embodiment of the invention where an e-juice vaporizer is used as a smoking apparatus, according to another embodiment of the invention.

In FIG. 20, another embodiment of sweatshirt pipe 10, is shown where smoking apparatus 12, is an e-juice or electronic vaporizer 62, with on/off button 64, chamber for e-juice 66, battery housing 68, and a securing element such as heat shrink material 60, for connecting the vaporizer to tube 26. Of course, other fastening means may also be used such as adhesives, bonding agents, matching groove-type fittings, tape, or the like.

Figure 21:
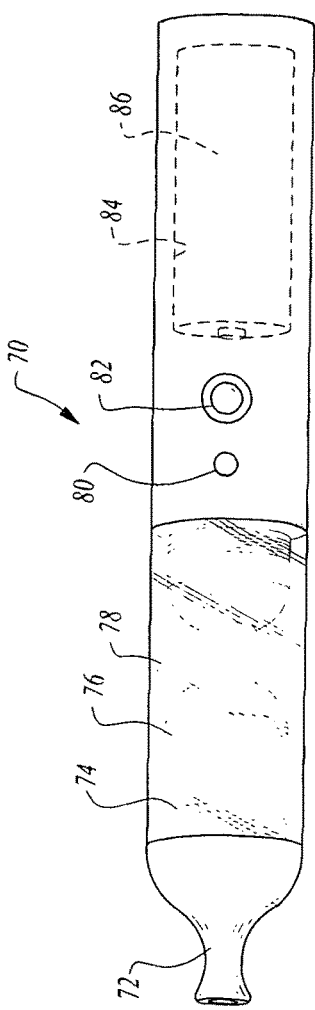
FIG. 21, shows another embodiment of the invention where an atomizer is used as a smoking apparatus, according to the invention.

In FIG. 21, an atomizer 70, is another attachment that may be used with sweatshirt pipe 10, and may be operably secured to tube 26 by a securing element. Atomizer 70, preferably includes mouthpiece 72, rubber 0-ring 74, atomizer 76, with glass or plastic cover 78, air hole 80, on/off button 82 and battery chamber 84, for a battery 86.

Figure 22:
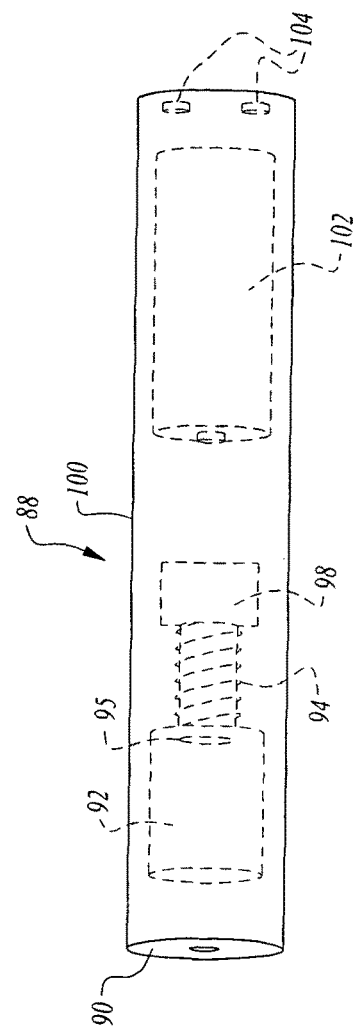
FIG. 22, shows another embodiment of the invention where a pre-filled e-cigarette is used as a smoking apparatus, according to the invention.

Referring now to FIG. 22, a pre-filled type e-cigarette 88, is shown as another attachment that may be used as a smoking apparatus in sweatshirt pipe 10. By securing e-cigarette 88, in tubing 26, the user may enjoy a pre-filled e-cigarette. In FIG. 22, e-cigarette 88, is shown with mouthpiece 90, a cartridge 92, with nicotine dissolved in propylene glycol or other agents as desired, heater coil 94, sensor 95, for detecting when the user inhales, microprocessor 98, for control of heater and light, battery housing 100, for battery 102, and led lights 104, which light up when the user inhales on the cigarette.

In operation and use, the present invention provides a sweatshirt pipe 10, which is a novel new type of clothing. Sweatshirt pipe 10, of the present invention enables the user to smoke tobacco out of a sweatshirt, or other article of clothing. It is constructed using high temperature resistant materials, while maintaining the look of a normal sweatshirt. Smoking apparatus 12, is constructed through the drawstring of the sweatshirt. Smoking apparatus 12, is preferably constructed by running high temperature tubing through the drawstring of the hood or the sweatshirt, or other article of clothing. The tubing 26 can be covered with drawstring material, which enables it to look like a conventional sweatshirt. The covering can be made with many different materials, including cotton, polyester, cotton-polyblends, fiberglass, carbon fiber, aramid, and the like. The tubing may be inserted into a covering or can be pre-made with covering. The tubing may be made of silicone, PVC, Tygon or other high temperature resistant tubing. Tubing 26, is connected to a smoking bowl 34, on one end into which the tobacco can be placed. The smoking bowl piece can be constructed out of glass, metal, wood, clay, bone, composite, or other high temperature resistant materials. Smoking bowl piece 34, may be provided in a wide variety of shapes and designs, and is preferably configured to look like a normal part of the sweatshirt 10, however, it may be alternatively be shaped to be noticed and extravagant. The other end of tubing 26, is connected to mouthpiece 30, which may be constricted of the same materials as the smoking bowl piece. Mouthpiece 30, is shaped to conform to the users mouth and can bed made to match the smoking bowl piece in appearance. Alternatively, mouthpiece 30, may be made to look different from smoking bowl piece 34, and both may be provided in various colors and configurations.

In other embodiments, as described herein, the sweatshirt pipe 10, may use other attachments as a smoking apparatus such as a vaporizer, an atomizer, an e-cig or electronic cigarette, a pre-filled e-cigarette, or other smoking apparatus used for smoking tobacco, concentrates of tobacco, and other substances and concentrates thereof.

Smoking apparatus 12, may be removed from sweatshirt 10, during washing. It can easily be pulled through the aperture 19, in the hood or collar, and can later be reinserted with ease. Smoking apparatus 12, is preferably held in place by stitching 17, running the perimeter of the hood or collar, or otherwise attached using mechanical fasteners, such as clips, clamps, or adhesives, for example. Smoking apparatus 12, is easily adapted and used with many different sweatshirt and jacket designs, or in other articles of clothing. If an article of clothing has any sort of drawstring system, the smoking apparatus 12, can easily be installed and used.

Additional advantages and modification will readily occur to those skilled in the art. The invention in its broader aspects is, therefore, not limited to the specific details, representative apparatus and illustrative examples shown and described. Accordingly, departures from such details may be made without departing from the spirit or scope of the applicant's general inventive concept.

What is claimed is:

1. A hooded sweatshirt, comprising:
a garment body having a neck opening and sleeves;
a hood, adapted to be worn over and configured to a user's head, is coupled with said body, said hood having a channel around the perimeter of said hood;
an elongated cord removably positioned inside said channel for tightening said hood;
a hollow tube positioned inside said elongated cord, said tube having a first end and a second end, said first end having a mouthpiece, and said second end having a smoking apparatus; and
a securing element coupling with said second end and said smoking apparatus to form an airtight seal between said second end and said smoking apparatus such that said mouthpiece is in gaseous communication with said smoking apparatus via said hollow tube, wherein the securing element is selected from the group consisting of silicone tapes, sealants, adhesives, heat shrinking tubing strips, fasteners, and metal wire wraps.

2. The hooded sweatshirt of claim 1, wherein said hooded sweatshirt is composed of a heat resistant material.

3. The hooded sweatshirt of claim 1, wherein said hollow tube is composed of a heat resistant material.

4. A hooded sweatshirt, comprising:
a garment body having a neck opening and sleeves;
a hood, adapted to be worn over and configured to a user's head, is coupled with said garment body, said hood having a channel around the perimeter of said hood;
an elongated cord removably positioned inside said channel for tightening said hood;
a hollow tube positioned inside said elongated cord, said tube having a first end for securing with a mouthpiece thereto and having a second end for securing a smoking apparatus thereto; and
an airtight seal formed between said second end and said smoking apparatus such that said mouthpiece is in gaseous communication with said smoking apparatus via said hollow tube.

5. The hooded sweatshirt of claim 4, wherein said hooded sweatshirt is composed of a heat resistant material.

6. The hooded sweatshirt of claim 4, wherein said hollow tube is composed of a heat resistant material.

7. An article of clothing, comprising:
a garment body having a neck opening and sleeves;
a hood coupled with said garment body, said hood having a channel around the perimeter of said hood;
an elongated cord removably positioned inside said channel for tightening said hood around a user's head or neck;
a hollow tube positioned inside said elongated cord, said tube having a first end operably secured with a mouthpiece and having a second end operably secured with a smoking apparatus; and
an airtight seal formed between said second end and said smoking apparatus such that said mouthpiece in gaseous communication with said smoking apparatus via said hollow tube.

8. The article of clothing of claim 7, wherein said article of clothing is composed of a heat resistant material.

9. The article of clothing of claim 7, wherein said hollow tube is composed of a heat resistant material.

* * * * *